United States Patent [19]

Lee

[11] Patent Number: 5,368,567
[45] Date of Patent: Nov. 29, 1994

[54] DILATATION BALLOON CATHETER WITH INFUSION LUMEN

[75] Inventor: Jeffrey A. Lee, Plymouth, Minn.

[73] Assignee: Schneider (USA) Inc., Plymouth, Minn.

[21] Appl. No.: 104,422

[22] Filed: Aug. 9, 1993

Related U.S. Application Data

[63] Continuation of Ser. No. 919,800, Jul. 27, 1992, abandoned.

[51] Int. Cl.$^5$ ............................................. A61M 29/00
[52] U.S. Cl. .................................... 604/102; 604/96; 606/194
[58] Field of Search .................. 604/96, 102, 280; 606/192, 194; 128/656–658, 772

[56] References Cited

U.S. PATENT DOCUMENTS

| | | |
|---|---|---|
| 4,748,979 | 6/1988 | Hershenson . |
| 4,748,982 | 6/1988 | Horzewski et al. .............. 606/192 |
| 4,762,129 | 8/1988 | Bonzel . |
| 4,771,777 | 9/1988 | Horzewski et al. .............. 606/194 |
| 4,771,782 | 9/1988 | Millar ................................ 128/637 |
| 4,784,636 | 11/1988 | Rydell ................................ 604/22 |
| 4,850,358 | 7/1989 | Millar ................................ 128/637 |
| 4,857,045 | 8/1989 | Rydell ................................ 604/22 |
| 4,909,258 | 3/1990 | Kuntz et al. ...................... 128/658 |
| 4,944,745 | 7/1990 | Sogard et al. .................... 606/194 |
| 4,955,895 | 9/1990 | Sugiyama et al. ................ 606/194 |
| 4,988,356 | 1/1991 | Crittenden et al. ............... 606/192 |
| 5,135,535 | 8/1992 | Kramer ............................. 606/194 |
| 5,137,513 | 8/1992 | McInnes et al. .................. 604/96 |
| 5,154,725 | 10/1992 | Leopold ............................ 606/194 |
| 5,156,594 | 10/1992 | Keith ................................ 604/96 |

FOREIGN PATENT DOCUMENTS 9217236 10/1992 WIPO .
9220397 11/1992 WIPO .

OTHER PUBLICATIONS

Marketing literature by Mansfield.

*Primary Examiner*—C. Fred Rosenbaum
*Assistant Examiner*—Corrine Maglione
*Attorney, Agent, or Firm*—Peter C. Richardson; Lawrence C. Akers; Philip C. Strassburger

[57] ABSTRACT

This disclosure is directed to the design of a dilatation catheter having two or more associated fluidcarrying tubes, the operative or distal end of one of which supplies fluid to inflate an expansible balloon and the operable or distal end of the other of which supplies an injectable dye or contrast enhancing fluid adjacent the proximal end of the balloon.

4 Claims, 2 Drawing Sheets

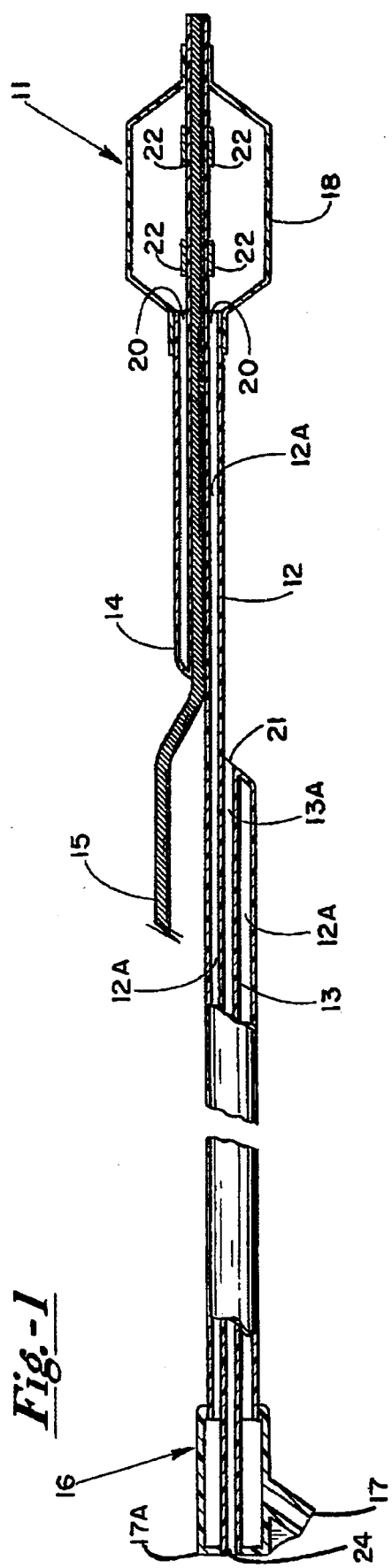

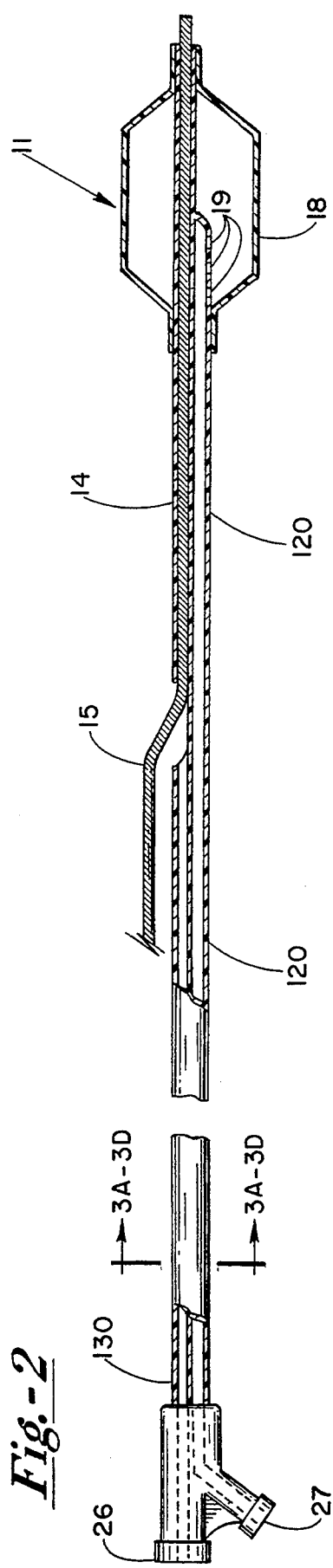

DILATATION BALLOON CATHETER WITH INFUSION LUMEN

This is a continuation of copending application Ser. No. 07/919,800, filed on Jul. 27, 1992 now abandoned.

BACKGROUND OF THE INVENTION

I. Field of the Invention

This invention is directed generally to intravascular catheters, and more particularly to the design of a dilatation catheter having a pair of associated fluidcarrying tubes, the operative or distal end of one of which supplies fluid to inflate an expansible balloon and the operable or distal end of the other of which supplies an injectable dye or contrast enhancing fluid adjacent the proximal end of the balloon.

II. Description of the Related Art

Dilatation catheters of the general class of the present invention are well known and generally described in references such as the American Journal of Cardiology, Volume 49, Apr. 1, 1982, pages 1216-1222. They are basically employed to enlarge constrictions in larger vessels or arteries, or even other internal cavities by employing a precisely placed inflatable balloon device to compress plaque or other obstructing material against the arterial wall or the outer surface of the cavity of interest thereby reopening a larger channel for blood flow or the like. This method of treatment of stenotic lesions in the vascular system is known as transluminal balloon angioplasty. The procedure involves the use of an elongated, flexible, plastic catheter having an inflatable expander member or balloon proximate its distal tip. The catheter describes a tubular lumen suitable to conduct an amount of fluid introduced from without the body to and from the balloon to accomplish inflation and deflation of the balloon as required. One such device is illustrated and described in U.S. Pat. No. 4 762 129. The system is introduced at an appropriate site in the vascular system, commonly in the femoral artery, and routed through the system using a guide wire to the site of the lesion of interest to be treated. Once the deflated balloon is positioned in the desired relationship to the lesion, the appropriate fluid is introduced into the proximal end of the catheter and flows to inflate the balloon which, in turn, compresses the stenotic lesion against the wall of the blood vessel.

In order for the balloon to be precisely positioned with respect to the stenosis to be compressed and the result easily evaluated, a contrast medium or dye is utilized to enhance the contrast at the site so that the scene can be viewed with greater resolution by the operator of the device. Normally, this involves injecting an amount of contrast fluid or dye material into the femoral artery and waiting until the diluted dye makes its way through the vascular system to the site of the stenotic lesion. There is a significant time delay between the time of injection and the corresponding effect on the image viewed on the fluoroscope. Because of the dilution effect, it also requires the injection of an additional amount of fluid consistent with the need to circulate the fluid through the vascular system to the site. Adjustments in concentration also require time and may lack the desired accuracy or control. It would represent a great improvement in the art if the appropriate contrast fluid or dye could be introduced near the distal end of the catheter proximate to the balloon member and the stenotic lesion. This would save a great deal of the time spent waiting for the fluid to circulate, reduce the amount of contrast fluid required and increase the control over the predictable result of dye addition.

SUMMARY OF THE INVENTION

Problems associated with remotely applying the proper amount of contrast medium to the vicinity of the stenotic lesion of interest in order to enhance visibility with respect to the operation of a dilatation catheter are solved by the structures contemplated by the present invention. Previous dilatation catheters contemplated a single operative, elongated hollow lumen for conducting the fluid utilized to inflate the balloon.

The present invention, on the other hand, involves the addition of a second operative elongated lumen substantially co-extensive with the balloon inflating lumen for conveying the contrast enhancing fluid dye, or the like, directly to the vicinity of the stenotic lesion to be treated. The particular form assumed by the two fluid-conducting elongated, hollow tubular structures or lumens may be co-axial, a spaced parallel biluminal arrangement or any other such integral or proximate satisfactory arrangement.

The guide wire associated with the dual fluid-carrying catheter system of the invention may be any compatible suitable arrangement. A Monorail TM system is preferred because it requires only a relatively short, hollow tube section which is open at both ends and adapted to receive a guide wire in a sliding fit and which traverses the interior of the expandable balloon from a point just beyond the distal end to beyond the proximal end of the balloon such that the guide wire needs to engage the catheter system only in the precise area where maximum control is required. This eliminates the need for a guide wire lumen co-extensive with the catheter system. A Monorail TM system is also disclosed in detail in the above-referenced U.S. Pat. No. 4 762 129 and to the extent necessary, specified details may be incorporated herein by reference.

The contrast medium conducting, hollow tube lumen has a distal opening for injecting the contrast medium preferably situated a short distance from the proximal end of the expandable balloon so that a maximum visual enhancement occurs at the site of the angioplasty treatment of the stenotic lesion. The short lumen engaging the guide wire with respect to the use of the Monorail TM guide wire system preferably begins adjacent the distal opening of the contrast medium lumen just beyond the distal opening so that the system contains no more than two spaced parallel lumens at any particular point. The majority of the length of the catheter with respect to a biluminal configuration may be provided with an additional sheathing lumen which encompasses both operating lumens to facilitate passage of the catheter system.

In operation, the guide wire is first introduced, normally into the femoral artery, through an introducer or guide catheter in a well-known manner and passed through the vascular system until it reaches the proper coronary or other artery, etc., or other site of the stenotic lesion of interest. The guide wire is normally thrust a small distance past the lesion to facilitate later maneuvering of the dilatation catheter. The dilatation catheter is then introduced onto the proximal end of the guide wire outside of the body and advanced through the guide catheter or anatomy and along the guide wire until it reaches the site for the angioplasty procedure. With the immediate availability of contrast enhancing fluid through the dual lumen system, contrast fluid may be introduced at any point along the path taken by the dilatation catheter as needed, and can be precisely placed very close to the site of the stenotic lesion in any amount required to enhance the operator's visibility.

BRIEF DESCRIPTION OF THE DRAWINGS

In the drawings, wherein like numerals are utilized to designate like parts throughout the same;

FIG. 1 shows one embodiment of the catheter of the invention broken, partly in section and with parts cut away to illustrate the plurality of lumens involved;

FIG. 2 is similar to FIG. 1 showing an alternate embodiment; and

FIGS. 3A-3D are enlarged sectional representations of various illustrative configurations in accordance with the dual lumen system of the invention.

DETAILED DESCRIPTION OF THE INVENTION

The invention will now be illustrated with reference to the embodiments represented by the drawings which are intended to be representative of the examples which may encompass the invention but are not designed to limit the scope of the invention in any manner. In FIG. 1, both the posterior and anterior portions of a dilatation catheter are represented. The dilatation catheter is designed to be advanced through the vascular system of a patient to position a balloon shown inflated at 11 at the site of a stenotic lesion to be treated. The catheter system includes a pair of elongated, coaxial hollow tubes 12 and 13, describing longitudinal hollow lumens 12A and 13A, respectively, and a relatively short, hollow tube 14, describing a lumen adapted to receive a guide wire 15 in a manner to be described. At the proximal end of the system, access is provided to the lumens 12A and 13A of tubes 12 and 13 via a T-member or similar fitting 16 containing a pair of separate access ports 17 and 17A. The balloon member consists of an inflatable envelope 18 which is sealingly connected to the tube member 14 at its distal end and sealingly connected to the dual tubes 12 and 14 at its proximal end. The fact that the tube 14 passes entirely through the balloon 11 allows the dilatation catheter assembly to be readily slipped on the guide wire 15 as desired.

The separate continuous hollow lumens 12A and 13A are configured such that a fluid introduced at the proximal access port 17 travels the length of the continuous lumen 12A and can be introduced to inflate the balloon through a plurality of openings as at 19 (FIG. 2) or at the end of the lumen at 20. Likewise, contrast enhancing medium fluid introduced at the proximal end port 24 (FIG. 1) or at 26 (FIG. 2) traverses the length of the tube 13 and may be injected close to the balloon 11 through open port 21. The catheter system can be further provided with radiopaque marker bands such as illustrated at 22 to further enhance tracking of the balloon member 11 through the vascular system and at the site of the procedure.

FIG. 2 depicts a dilatation catheter system similar to that of FIG. 1 except that in the biluminal system of FIG. 2, placement of the tubes 120 and 130 is modified so that tube 120, for example, is connected to proximal access 27 and tube 130, to proximal access 26; and, more importantly, the tube 130 is aligned axially with the guide wire tube 14 to produce a slightly more streamlined system.

As noted in FIGS. 3A-3D, the associative or integral parallel relationship of the two tubes 120 and 130 may take on a variety of configurations. These are represented by numbers 13B-E and 12B-E with 12B and 13B, 12D and 13D, and 12E and 13E representing three possible biluminal configurations. 12C and 13C are encapsulated in a further sheathing member 30 which surrounds and contains both to facilitate passage of the biluminal configuration through the vascular system. It will be appreciated from the representative illustrations that any practical combination containing a pair of separate but parallel lumens of the size desired which would occur to those skilled in the art might be used. The dye lumen, however, is normally larger in diameter than the inflation lumen. The same choice of arrangements, of course, is available with respect to the guidewire lumen 14.

With respect to one successful embodiment similar to FIG. 2, the overall dimension of the biluminar tube as at 30 was approximately 0.073"OD which is small enough to readily traverse coronary arteries or the like to accomplish the angioplasty procedure. The typical guide wire is approximately 0.035" in diameter so the combination guide wire and inflation lumen section is also well within a size that can readily be accommodated. Of course, while the above dimensions refer to a specific model of catheter, it is contemplated that the invention can be used in catheter devices having dimensions both larger and smaller than those specifically stated.

When the system is operated, the guide wire is first introduced through a guide catheter into the arterial system of the patient, typically through the femoral artery, and advanced through the vascular system until the guide wire tip reaches a point just beyond the stenotic lesion of interest. At this point, a portion of the guide wire, of course, still extends through the guide catheter to a point outside the body. The balloon 11 can then be threaded over the end of the wire so that the wire is passed through the hollow lumen 14 and the biluminal catheter system is then advanced over the wire through the vascular system to the site of the constriction near the tip of the guide wire.

In accordance with the invention, a dye or other type of contrast enhancing medium can be introduced into the lumen 13 at any point in the procedure if such is needed near the location of the balloon. One great advantage of this system is that contrasting enhancement medium in any desired amount can be directed almost instantaneously to the spot of the constriction when the balloon reaches the constriction. This facilitates the illumination of site to make control of the manipulation of the devices during the procedure much easier. The ready availability of the dye material directly at the site represents a decided improvement in control and accuracy with respect to the administration of the angioplasty procedure which enhances the probability of success. It removes the guess work associated with having to introduce fluid at the point of catheter introduction and waiting for the fluid to traverse the vascular system before it reaches the site of the procedure possibly in a highly diluted state.

It will be appreciated that both sections of the catheter system utilizing biluminal construction may be very similar with respect to the cross-section and although the illustrations of FIGS. 3A-3D show the combination of lumens 12 and 13, the same holds true for the cross-section with respect to lumens 12 and 14; and, as such, these need not further be illustrated. The encapsulating material as at 30 may be a type of heat-shrinkable polymeric material or the like of minimal thickness and of desirable strength to properly retain the spaced parallel tubes 12 and 13 or 12 and 14. The dual lumens may be formed in the same tube, as in FIGS. 3A and 3D, or co-axially disposed, as in FIG. 1.

This invention has been described herein in considerable detail in order to comply with the Patent Statutes, and to provide those skilled in the art with the information needed to apply the novel principles and to construct and use such specialized components as are required. However, it is to be understood that the invention can be carried out by specifically different equipment and devices, and that the various modifications, both as to the equipment details and operating procedures, can be accomplished without departing from the scope of the invention itself.

What is claimed is:

1. A dilation catheter comprising
   (a) a shaft having a proximal end and a distal end, the shaft defining an inflation lumen for allowing an inflation fluid to pass therethrough, a guidewire lumen for allowing a guidewire to pass therethrough and an infusion lumen for allowing a contrast enhancing medium fluid to pass therethrough;
   (b) a balloon having a proximal end and a distal end, the balloon defining a balloon interior and being mounted adjacent the distal end of the shaft;
   (c) a first inflation port at the proximal end of the shaft, the first inflation port being in communication with the inflation lumen;
   (d) a second inflation port in communication with the inflation lumen and the balloon interior;
   (e) a first guidewire port spaced proximally from the proximal end of the balloon in communication with the guidewire lumen;
   (f) a second guidewire port at the distal end of the shaft in communication with the guidewire lumen;
   (g) a first infusion port at the proximal end of the shaft for receiving the contrast enhancing medium fluid, the first infusion port being in communication with the infusion lumen; and
   (h) a second infusion port spaced distally from the proximal end of the shaft and spaced proximally from the first guidewire port for allowing the contrast enhancing medium fluid to exit the dilation catheter while the guidewire is disposed in the guidewire lumen, the second infusion port being in communication with the infusion lumen and wherein the first guidewire port is located on the side of the shaft opposite the second infusion port so that the guidewire does not interfere with the infusion of the contrast enhancing medium fluid.

2. The dilation catheter of claim 1 wherein the inflation lumen and the infusion lumen are parallel.

3. The dilation catheter of claim 1 wherein the inflation lumen and the infusion lumen are formed as integral separate parallel lumens contained in a single member.

4. The dilation catheter of claim 1 wherein the infusion lumen has a larger diameter than the inflation lumen.

* * * * *